United States Patent [19]

Leder et al.

[11] Patent Number: 5,554,499
[45] Date of Patent: Sep. 10, 1996

[54] DETECTION AND ISOLATION OF LIGANDS

[75] Inventors: Philip Leder, Chestnut Hill; John G. Flanagan, Brookline, both of Mass.

[73] Assignee: President and Fellows of Harvard College, Cambridge, Mass.

[21] Appl. No.: 306,255

[22] Filed: Sep. 14, 1994

Related U.S. Application Data

[60] Continuation of Ser. No. 945,514, Sep. 16, 1992, abandoned, which is a division of Ser. No. 593,764, Oct. 5, 1990, abandoned.

[51] Int. Cl.$^6$ ............... G01N 33/535; G01N 33/566; G01N 33/569; G01N 33/574
[52] U.S. Cl. ............... 435/5; 435/7.2; 435/7.21; 435/7.23; 435/7.24; 435/7.6; 435/7.8; 435/7.9; 435/21; 435/960; 435/963; 436/501; 436/824; 530/413; 935/47
[58] Field of Search ............... 435/5, 7.2, 7.21, 435/7.23, 7.24, 7.6, 7.8, 7.9, 21, 960, 963, 172.3; 436/501, 824; 530/413; 935/47

[56] References Cited

U.S. PATENT DOCUMENTS

| | | | |
|---|---|---|---|
| 4,542,096 | 9/1985 | Leder | 435/6 |
| 4,859,609 | 8/1989 | Dull et al. | 436/501 |
| 4,933,294 | 6/1990 | Waterfield et al. | 436/501 |
| 5,109,123 | 4/1992 | Reinherz et al. | 536/27 |
| 5,110,906 | 5/1992 | Maddon et al. | 530/350 |
| 5,116,740 | 5/1992 | Sarngodharan et al. | 435/70.4 |
| 5,126,433 | 6/1992 | Maddon et al. | 530/395 |
| 5,155,027 | 10/1992 | Sledziewski et al. | 435/69.7 |
| 5,156,949 | 10/1992 | Lucia et al. | 435/5 |
| 5,199,942 | 4/1993 | Gillis | 604/4 |

OTHER PUBLICATIONS

Young et al., Proc. Natl. Acad. Sci., USA, vol. 80, Issued Mar. 1983, pp. 1194–1198.
J. G. Flanagan et al, *Cell*, 63, 185–194, 1990.
Yarden, et al., *The EMBO Journal*, vol. 6, No. 11, pp. 3341–3351, 1987.

*Primary Examiner*—David Saunders
*Attorney, Agent, or Firm*—Fish & Richardson P.C.

[57] ABSTRACT

Disclosed is a method of isolating a ligand from a sample, the method including: providing a hybrid molecule including the receptor for the ligand covalently bonded to the first member of a specific binding pair; contacting sample with the hybrid molecule to form an affinity complex between the ligand and the hybrid molecule; and isolating the affinity complex using the second member of the specific binding pair. Also disclosed is a c-kit ligand, nucleic acid encoding such a ligand, and recombinant cells containing such nucleic acid. The c-kit ligand may be used to stimulate hematopoietic cell growth.

46 Claims, 5 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 67
        ( B ) TYPE: nucleic acid
        ( C ) STRANDEDNESS: single
        ( D ) TOPOLOGY: linear     ( x i ) SEQUENCE DESCRIPTION: SEQUENCE ID NO: 1:

```
GTACCAAGCT TACGTAAGAT CTTCCGGAAT CATCCCAGTT GAGGAGGAGA ACCCGGACTT      60

CTGGAAC                                                                67
```

( 2 ) INFORMATION FOR SEQ ID NO:2:

( i ) SEQUENCE CHARACTERISTICS:
        ( A ) LENGTH: 67
        ( B ) TYPE: nucleic acid
        ( C ) STRANDEDNESS: single
        ( D ) TOPOLOGY: linear     ( x i ) SEQUENCE DESCRIPTION: SEQUENCE ID NO: 2:

```
GCTTCTTGGC GGCACCCAGG GCCTCGGCTG CCTCGCGGTT CCAGAAGTCC GGGTTCTCCT      60
```

CCTCAAC 6 7

(2) INFORMATION FOR SEQ ID NO:3:

(i) SEQUENCE CHARACTERISTICS:
  (A) LENGTH: 41
  (B) TYPE: nucleic acid
  (C) STRANDEDNESS: single
  (D) TOPOLOGY: linear  (xi) SEQUENCE DESCRIPTION: SEQUENCE ID NO: 3:

CGCGAGGCAG CCGAGGCCCT GGGTGCCGCC AAGAAGCTGC A 41

(2) INFORMATION FOR SEQ ID NO:4:

(i) SEQUENCE CHARACTERISTICS:
  (A) LENGTH: 33
  (B) TYPE: nucleic acid
  (C) STRANDEDNESS: single
  (D) TOPOLOGY: linear  (xi) SEQUENCE DESCRIPTION: SEQUENCE ID NO: 4:

TGGGATGATT CCGGAAGATC TTACGTAAGC TTG 33

(2) INFORMATION FOR SEQ ID NO:5:

(i) SEQUENCE CHARACTERISTICS:
  (A) LENGTH: 29
  (B) TYPE: nucleic acid
  (C) STRANDEDNESS: single
  (D) TOPOLOGY: linear  (xi) SEQUENCE DESCRIPTION: SEQUENCE ID NO: 5:

GGTACCAAGC TTACGTAAGA TCTTCCGGA 29

DETECTION AND ISOLATION OF LIGANDS

This is a continuation of application Ser. No. 07/945,514, filed Sep. 16, 1992 now abandoned, which is a divisional of application Ser. No. 07/593,764 filed Oct. 5, 1990 now abandoned.

BACKGROUND OF THE INVENTION

The invention relates to the use of a specific affinity existing between two molecules to purify or identify another molecule.

There currently exists a variety of methods, materials, and approaches for the separation of a particular protein from the other components of a biological sample. One general approach exploits the non-specific affinity of a protein for a substrate. For example, proteins may be separated based upon their molecular charge using ion exchange chromatography. In ion exchange chromatography, protein mixtures are applied to an oppositely charged, chromatographic matrix (e.g., DEAE- or carboxymethyl-Sephadex), and the various proteins bind to the matrix by reversible, electrostatic interactions. The adsorbed proteins are eluted, in order of least to most strongly bound, by increasing the ionic strength or by varying the pH of the elution buffer.

Another general approach makes use of a protein's physical characteristics as a means of separation. For example, a protein may be separated based upon its size, using gel filtration. By this method, protein mixtures are applied to a gel-filtration column containing a chromatographic matrix (e.g., Sephadex, Bio-Gel, or Sephracryl) of defined pore size. Proteins are eluted, generally with an aqueous buffer, collected as individual chromatographic fractions and analyzed.

Both of the general approaches described above suffer from an inability, in most cases, to specifically isolate the protein to be purified from other proteins having similar physical characteristics.

A third general approach makes use of the specific affinity of a protein for a purifying reagent. A protein, for example, may be purified using an antibody specific for that protein. In one common application, the antibody is bound to a column substrate (e.g., Sepharose) and a high molecular weight antigen applied to the column. High molecular weight antigen molecules pass freely into and out of the pores and bind to antibodies covalently attached to the matrix. Bound proteins are then eluted by destabilizing the antigen-antibody complex, e.g., by brief exposure to high pH or low pH buffers. Antibodies are also used to purify proteins by immunoprecipitation. Antigen-antibody complexes may be precipitated following aggregation, or alternatively, antibodies may be covalently linked to Sepharose and immunoaffinity complexes isolated by centrifugation. In either method, the protein of interest is then released from the complex and analyzed, generally by polyacrylamide gel electrophoresis. Immunoprecipitation methods rely on optimizing specific antigen-antibody complex formation while minimizing non-specific interactions; as such, in some instances, the protein of interest is not precipitated; in other instances, the precipitate contains the desired protein significantly contaminated with other proteins. In addition, this method requires that an antibody specific for the protein of interest be available or that it can be prepared.

SUMMARY OF THE INVENTION

In general, the invention features a method of isolating a ligand, preferably, a polypeptide ligand, from a sample, including providing a hybrid molecule including the receptor for the ligand covalently bonded, preferably by a peptide bond, to the first member of a specific binding pair; contacting the sample with the hybrid molecule to form an affinity complex between the ligand and the hybrid molecule; and isolating the affinity complex using the second member of the specific binding pair. The invention further features a method of detecting a ligand, preferably, a polypeptide ligand, in a sample including: providing a hybrid molecule including an oncogene-encoded receptor for the ligand covalently bonded, preferably, by a peptide bond, to the first member of a specific binding pair; contacting the sample with the hybrid molecule to form an affinity complex between the ligand and the hybrid molecule; and detecting the affinity complex using the second member of the specific binding pair.

The invention also provides a method for determining the ability of a molecule to interfere with the binding of a ligand, preferably, a polypeptide ligand, to a receptor, preferably, a polypeptide receptor, including: contacting the ligand with the molecule and with a hybrid molecule including the receptor covalently bonded, preferably by a peptide bond, to the first member of a specific binding pair; allowing an affinity complex between the hybrid molecule and the ligand to form; and measuring the affinity complex using the second member of the specific binding pair, the measurement being an inverse measure of the ability of the molecule to interfere with binding.

In various preferred embodiments the ligand can be soluble, e.g., secreted, or insoluble, e.g., bound to a cell; the affinity complex may be contacted with a cross-linking agent to cross-link the ligand to the receptor; the receptor, which is preferably a polypeptide, can be a cell surface receptor, e.g., an oncogene-encoded receptor, e.g., a c-kit receptor, e.g., a mouse c-kit receptor, and preferably, the human c-kit receptor, or a viral receptor, e.g. an HIV envelope protein receptor, e.g., CD4; the receptor includes only the soluble, and not the insoluble, portion of an insoluble polypeptide; the specific binding pair includes an enzyme e.g., secreted placental alkaline phosphatase (SEAP), and a substrate or substrate analog of the enzyme, or an antibody and the antigen to which the antibody binds, e.g., SEAP and an antibody that binds to SEAP. In preferred embodiments of methods for detecting a ligand, the detection of an affinity complex allows determination of the distribution of the ligand in the sample; and, the sample is a tissue section or a blot, e.g., a Western blot.

The invention also includes a purified mammalian, preferably mouse, more preferably human, protein ligand which binds a c-kit receptor. In various preferred embodiments the ligand includes a 41 kD and a 55 kD component; the ligand is derived from a fibroblast cell; and the ligand is a cell surface molecule. Nucleic acid encoding such a mammalian protein ligand, a vector containing such a nucleic acid, and a recombinant cell containing such nucleic acid.

Finally, the invention features a method of stimulating proliferation of hematopoietic cells, involving contacting hematopoietic cells with a growth-stimulatory amount of a c-kit ligand, preferably, the human c-kit ligand. In preferred embodiments, the ligand is presented on the surface of a cell.

Ligand and receptor, as used herein, means a pair of biological molecules that have a specific affinity for each other. One member of the receptor-ligand pair must be localized on a surface of a membrane, and preferably on a surface of the plasma membrane, at some point in its in vivo existence. Preferably, the affinity arises by virtue of the members of the receptor-ligand pair possessing complementary three-dimensional structures, e.g., as seen in the relationship between an enzyme and its substrate. Within a given receptor-ligand pair, either member may be considered to be the ligand or the receptor. Examples of ligand-receptor pairs include all of the following: a cell surface receptor (e.g., a molecule that transmits a signal, e.g., across a cell membrane, when bound to its ligand) and its ligand, e.g., an oncogene-encoded receptor and its ligand or a growth factor and its receptor, e.g., a lymphokine and its receptor, e.g., an interleukin and its receptor; an enzyme and its substrate; an enzyme and a specific inhibitor or other non-catalyzable substrate of the enzyme; a hormone and its receptor; a first subunit of a multimeric protein and a second subunit of the multimeric protein, e.g., two subunits of an immunoglobin molecule; a polypeptide portion of a protein and a non-peptide cofactor of the protein; a molecule involved in cellular adhesion (e.g., a carbohydrate involved in cell adhesion; a cadherin; a cell adhesion molecule (CAM), e.g., cell-CAM, neural N-CAM, or muscle N-CAM; a laminin; a fibronectin; or an integrin) and the molecule to which it binds, which may or may not be a cellular adhesion molecule; a first component of an organelle, the mitotic or meiotic apparatuses, or other subcellular structure, that displays a specific interaction with a second component of the same structure or a related structure; a lectin and a carbohydrate; a toxin and its receptor, e.g., diphtheria toxin and its cell surface receptor; a component of a virus and its cell surface receptor; or, an IgE molecule and an IgE receptor, e.g., the IgE receptor found on mast cells, or any other Ig molecule and its receptor (where receptor does not include the antigen against which the antibody molecule is directed, i.e., an antibody and its antigen are not within the definition of a receptor and its ligand, as used herein). A first strand of nucleic acid and a second strand complementary to the first are not within the definition of a ligand and its receptor.

Specific binding pair, as used herein, means any pair of molecules, including a first and a second member, which have a specific affinity for each other. Examples of specific binding pairs include ligands and receptors, as defined above, avidin and biotin, and antibodies and their antigens.

Substrate analog, as used herein, means a molecule which is bound, but not acted upon, e.g., cleaved, by an enzyme.

A human analog of a mouse ligand, as used herein, means a human ligand Which: can specifically bind the receptor for the mouse ligand of which it is an analog; or can specifically bind to the human analog of the mouse receptor; or is encoded by a gene which bears sufficient homology to the gene encoding the mouse ligand of which it is an analog to allow the human gene to be isolated by its homology to the mouse gene.

Polypeptide, as used herein, means any chain of amino acids. Purified protein or polypeptide, as used herein, means a preparation in which the protein or polypeptide is purified at least 100-fold and is substantially free of other proteins, carbohydrates, and lipids with which it is naturally associated.

A purified nucleic acid sequence, as used herein, is a nucleic acid sequence which has been separated from other sequences with which it is naturally associated.

C-kit ligand, as used herein, means a protein which binds specifically to a c-kit-encoded receptor protein.

Viral receptor, as used herein, means a protein on a host cell surface to which a virus attaches.

Derived from a fibroblast cell, as used herein, means naturally produced or recombinantly produced by a fibroblast cell.

Blot, as used herein, means a solid support (e.g., a nitrocellulose filter) on which a ligand has been immobilized. Tissue section, as used herein, means a sample of cells which have been explanted from an organism and which have been immobilized on a solid support.

The invention provides advantages over a wide variety of techniques used for the capture or assay of a particular molecule, for the determination of the distribution of a ligand in situ, and for competitive binding experiments, e.g., for competitive inhibition experiments. The methods are rapid and easy to perform. A hybrid molecule can be produced quickly and at a relatively high concentration. The interaction between the ligand and receptor members of the binding pair are very specific. The hybrid molecules used in methods of the invention contain one member of a specific binding pair and thus require fewer steps than many sandwich assays. Finally, the methods do not require any knowledge about the identity of the ligand to be captured or assayed; this provides an advantage over traditional immunoprecipitation techniques for which antibodies to the desired protein must be available or prepared.

Other features and advantages of the invention will be apparent from the following description of the preferred embodiments, and from the claims.

DESCRIPTION OF THE PREFERRED EMBODIMENTS

The drawings will first briefly be described.

Drawings

CONSTRUCTION OF A GENE ENCODING A LABELLED SOLUBLE MOLECULAR AFFINITY REAGENT; THE APtag-KIT FUSION GENE The APtag-KIT fusion gene was constructed by inserting a DNA sequence encoding a portion of the c-kit gene product into plasmid APtag-1.

The APtag-1 vector was constructed as follows: Plasmid pBC12/PL/SEAP was digested with PstI in the presence of 7 μg/ml ethidiumbromide to favor the production of singly-cut linear products. The singly-cut 5.2 kb product was then isolated following agarose gel electrophoresis, digested with BglII, and a 5.0 kb fragment, termed Fragment 31, isolated by a second round of agarose gel electrophoresis. A second plasmid, pIRV-CMVact, was digested with BamHI and Asp718I and a 0.6 kb fragment, termed Fragment 32, containing a Moloney murine leukemia virus LTR (Genbank Accession No. J02255, J02256, J02257), was isolated following agarose gel electrophoresis. Four oligonucleotides of sequence:

G TAC CAA GCT TAC GTA AGA TCT TCC GGA ATC ATC CCA GTT GAG GAG GAG AAC CCG GAC TTC TGG AAC,

G CTT CTT GGC GGC ACC CAG GGC CTC GGC TGC CTC GCG GTT CCA GAA GTC CGG GTT CTC CTC CTC AAC,

CGC GAG GCA GCC GAG GCC CTG GGT GCC GCC AAG AAG CTG CA, and

TGG GAT GAT TCC GGA AGA TCT TAC GTA AGC TTG were synthesized by standard techniques, and isolated and purified by polyacrylamide/urea gel electrophoresis.

The four oligonucleotides were annealed together in 10 mM NaCl by cooling from 95° C. to 37° C. in a water bath over a period of approximately 3 hrs. The resultant double-stranded DNA fragment was ligated, in a three-piece ligation, to Fragment 31 and Fragment 32 to produce the plasmid, APtag-1.

In APtag-1, the first codon of the mature SEAP protein (Berger et al., *Proc. Natl. Acad. Sci. USA* 84:4885, 1987, hereby incorporated by reference, Berger et al., *Gene* 66:1, 1988, hereby incorporated by reference) is immediately preceded by the nucleotide sequence:

| KpnI | HindIII | SnaBI | BglII | BspMII |
|------|---------|-------|-------|--------|
| GG TAC CAA GCT TAC GTA AGA TCT TCC GGA | | | | |

Figure 1:
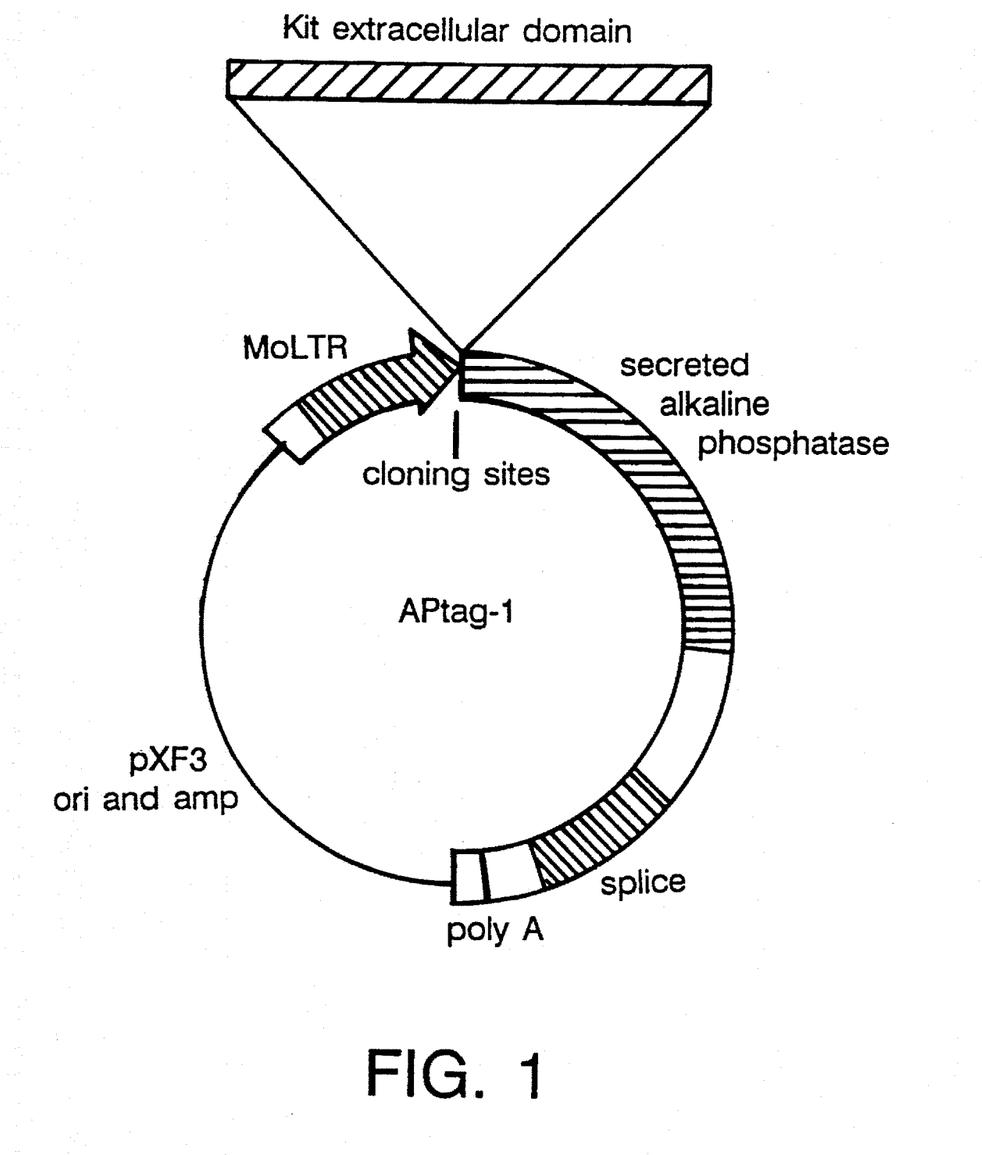
FIG. 1 is a diagrammatic representation of the plasmid APtag-KIT-1.

This sequence includes cloning sites into which genes or gene fragments may be inserted to produce an APtag fusion protein (see FIG. 1).

The structure of APtag-1 allows for the production of a fusion protein with an enzyme tag at its C-terminal end. The KpnI site shown above marks the 3' end of a 625 bp ClaI to KpnI fragment of the Moloney murine leukemia virus LTR; this fragment is flanked on its 5' side by sites for SnaBI, EcoRI, SalI and ClaI. The remainder of APtag-1 is the same as nucleotides 62 to 5212 of pBC12/PL/SEAP. Thus the relevant portion of APtag-1 includes, in the following order: restriction enzyme sites SnaBI, EcoRI, SalI, and ClaI; a 625 bp ClaI-KpnI fragment of the Moloney mouse leukemia virus LTR (Genebank Accession Nos. J02255, J02256, J02257); the restriction enzyme sites KpnI, HindIII, SnaBI, BglII, and BspMII; and nucleotides 62 to 5212 of plasmid pBC12/PLAP (Berger et al., *Gene* 66:1, 1988), including a sequence encoding amino acids 1 to 489 of secreted placental alkaline phosphatase, a 3'-intronic region and the polyadenylation site of the rat preproinsulin II gene (Lomedico et al., *Cell* 18:545, 1979, hereby incorporated by reference), the SV40 origin of replication, and the entire sequence of pXF3, a poison sequence-minus derivative of pBR322 (Hanahan et al., *J. Mol. Biol.* 166:557, 1983, hereby incorporated by reference; Cullen et al., *Cell* 46:973, 1986, hereby incorporated by reference). The Ig heavy chain promoter and enhancer, the CMV enhancer, or the Rous sarcoma virus LTR may, for example, be used in place of the Moloney murine leukemia virus LTR to direct expression of the hybrid protein; and an SV40 intron and splice site may, for example, be used in place of the rat preproinsulin sequence.

SEAP was chosen as the enzyme tag for a number of reasons, including the availability of a variety of indicator substrates for alkaline phosphatases, the high specific activity of the mammalian enzymes, the high stability, including stability to heat, of the placental isozyme, and the availability of isozyme-specific inhibitors that can be used to reduce background phosphatase activities (Berger et al., *Gene* 66:1, 1988; Harlow and Lane, *Antibodies: a laboratory manual*, Cold Spring Harbor Laboratory, Cold Spring Harbor, N.Y., 1988, hereby incorporated by reference; Zoellner and Hunter, *J. Histochem. Cytochem.* 37:1893, 1989, hereby incorporated by reference). In addition, proteolytic digestion studies indicated that both the N- and C-termini of the protein are dispensable for activity (Jemmerson et al. in *Human Alkaline Phosphatases*, T. Stigbrand & W. H. Fishman, Liss, N.Y., 1983, hereby incorporated by reference), making it likely that protein fusions at either end would leave the enzyme activity intact.

To generate a c-kit receptor fusion protein, the 5' end of a c-kit cDNA sequence, including sequences encoding the c-kit secretion signal peptide and the entire extracellular domain (i.e., ending immediately before the first hydrophobic amino acid of the transmembrane region,) was inserted into APtag-1.

To isolate a partial coding sequence for the receptor-encoding proto-oncogene, c-kit, first-strand cDNA was prepared from 4 μg of total mouse spleen RNA (Boehringer Mannheim cDNA kit, Boehringer Mannheim, Indianapolis, Ind.). Following phenol extraction and ethanol precipitation, one twentieth of this cDNA was amplified by PCR (Perkin-Elmer Cetus GeneAmp kit, Norwalk, Conn.) using primers based on the reported mouse c-kit cDNA sequence (Qiu et al., *EMBO J.* 7:1003, 1988, hereby incorporated by reference) and designed to flank the resultant PCR product with HindIII and BamHI sites. The resulting fragment of c-kit cDNA, extending from nucleotide 7 to 1585 of the published sequence and flanked by artificial sites for HindIII and BamHI, was inserted between the HindIII and BglII sites of APtag-1, yielding plasmid APtag-KIT-1. The encoded fusion protein contains the secretion signal peptide and the entire extracellular domain of c-kit (i.e., amino acid 1 to 519) fused to most of SEAP (i.e., amino acids 1 to 489) via a four amino acid linker, Gly-Ser-Ser-Gly, derived from the polylinker sequence.

Production of the APtag-KIT fusion protein

When APtag-KIT-1 was transfected into J558L myeloma cells, a protein of the expected size was produced: after stably-transfecting cells and immunoprecipitating the supernatant with a monoclonal antibody to human placental alkaline phosphatase, the fusion protein was seen as a single band migrating at 150 Kd. Unfused SEAP migrated at 67 Kd. Enzyme assays in solution demonstrated that the tag on the fusion protein retained its alkaline phosphatase activity.

The APtag-KIT fusion protein was produced in a mammalian cell line stably transfected with the APtag-KIT gene. The APtag-KIT-1 plasmid was linearized with ClaI and was co-transfected, along with the selectable marker plasmid pSV7neo (described in Murphy et al., *Proc. Natl. Acad. Sci. USA* 83:2939 (1986), hereby incorporated by reference), into J558L myeloma cells (ATCC accession no. TIB 6, Oi et al., *Proc. Natl. Acad. Sci USA* 80:825, 1983) using the electroporation technique described in Potter et al., *Proc. Natl. Acad. Sci.* 81:7161, 1984, hereby incorporated by reference. Cells were then grown in Dulbecco's Modified Eagle's Medium (DMEM) (Whittaker Bioproducts, Inc., Walkersville, Md.) containing 10% bovine calf serum (Hyclone Laboratories Inc., Logan, Utah), and after selection with 800 μg/ml G418 (Life Technologies Inc., Grand Island, N.Y.), approximately 100 neo® clones were screened for secretion of placental alkaline phosphatase activity. The alkaline phosphatase assay was performed by heating a portion of the supernatant at 65° C. for 10 min. to inactivate background phosphatase activity, and then measuring the $OD_{405}$ following incubation in a solution of 1M diethanolamine, pH9.8 (Sigma, St. Louis, Mo.), 0.5 mM $MgCl_2$, 10 mM L-homoarginine (a phosphatase inhibitor) (Sigma, St. Louis, Mo.), 0.5 mg/ml BSA (Sigma cat.no. A-7638, St. Louis Mo.) and 12 mM p-nitrophenyl phosphate (Sigma cat.no. 104–105, St. Louis, Mo.), prepared as a single 2X stock solution. The highest AP-expressing clone, termed J558.AK, produced up to 1.2 μg/ml of APtag-KIT fusion protein or up to 900 mU/ml of activity [1 unit of enzyme hydrolyzes 1 μmol/min of p-nitrophenyl phosphate at 37° C., Sigma catalogue, 1989, Sigma Chemical Company, St. Louis, Mo.]. J558.AK was used for production of the APtag-KIT fusion protein, although it was subsequently determined that NIH-3T3 cells, stably transfected with the APtag-KIT-encoding plasmid described above, could secrete up to 20 times more activity (i.e., 24 μg/ml of APtag-KIT fusion protein). A control cell line expressing unfused SEAP was produced by transfecting J558L with plasmid pBC12/CMV/SEAP using the techniques described above. The resultant clone, termed J558.AP, produced up to 360 mU/ml of activity. In an alternative method, plasmid pBC12/RSV/SEAP (Berger et al., *Gene* 66:1, 1988) may be used to direct expression of secreted placental alkaline phosphatase.

To determine the specific activity of the proteins, the concentration and molecular weight of APtag-KIT and SEAP in J558L supernatants were measured by metabolically labelling cell proteins with $^{35}$S-methionine (as described in Harlow and Lane, *Antibodies: A Laboratory Manual*, Cold Spring Harbor Laboratory, Cold Spring Harbor, N.Y., 1988) and immunoprecipitating the APtag-KIT and SEAP proteins from the supernatants using a monoclonal antibody to human placental alkaline phosphatase (as described below). Immunoprecipitated proteins were analyzed by electrophoresis on a 10% SDS/polyacrylamide gel, followed by Coomassie blue staining. The concentration and molecular weight of the recombinantly-produced proteins were determined by comparison with a known quantity of protein MW standards (available, e.g., from Bethesda Research Laboratories Inc., GIBCO/BRL, Grand Island, N.Y.). SEAP protein was found to be of the predicted MW of 67 KD; APtag-KIT protein was of the predicted MW of 150 KD. The specific activity of the proteins was calculated to be 750 U/mg and 1,500 U/mg for APtag-KIT and SEAP, respectively. The specific activities were thus indistinguishable on a molar basis, since the APtag-KIT protein is approximately twice as large as the SEAP protein. The specific activity estimate for SEAP is similar to the previously reported value of 2,000 U/mg (Berger et al., *Gene* 66:1, 1988).

The APtag-KIT protein was concentrated and purified as follows. Two liters of J558.AK supernatant was concentrated 10-fold by ultrafiltration (Amicon, Beverly, Mass) and then incubated with a 1 ml of monoclonal antibody to placental alkaline phosphatase (cat.no. A-018-02 Medix Biotech, Foster City, Calif.) which was coupled to CNBr-activated Sepharose 4B beads (Pharmacia, Piscataway, N.J.) by the techniques provided by Pharmacia, hereby incorporated by reference. The beads were then transferred to a column with a sintered base, and specifically bound protein was eluted from the beads with 144 mM NaCl, 1 mM $MgCl_2$, 1 mM $CaCl_2$, 50 mM sodium citrate pH 5.5, and immediately neutralized with 1M HEPES pH 8.0. The eluted protein was approximately 30% pure and had a specific activity of 300 U/mg. The APtag-KIT protein, isolated directly from cell supernatants, or concentrated and purified, appeared stable for several months when stored in tissue culture supernatant or neutralized eluant at 4° C.

Detection of KIT-specific ligand and characterization of the molecular affinity reagent-ligand interaction APtag-KIT binds specifically to cells that produce biologically active kit ligand.

Previous experiments reported by Fujita et al. (*Blood* 72:463, 1988) and the inventors (unpublished) have established that normal cultured mouse-derived mast cells, but not W/W$^v$ mutant cultured mouse-derived mast cells (i.e., cells harboring a defective kit receptor gene, Chabot et al., *Nature* 335:88, 1988, Geissler et al., *Cell* 55:185, 1988) grow on a layer of NIH-3T3 or Balb/c-3T3 fibroblasts; neither grow on L929 fibroblasts. These three fibroblast lines were therefore tested for the production of a factor that would bind specifically to the APtag-KIT fusion protein; also tested were COS cells, a line of monkey fibroblasts that were found not to support growth of mouse mast cells.

Figure 2:
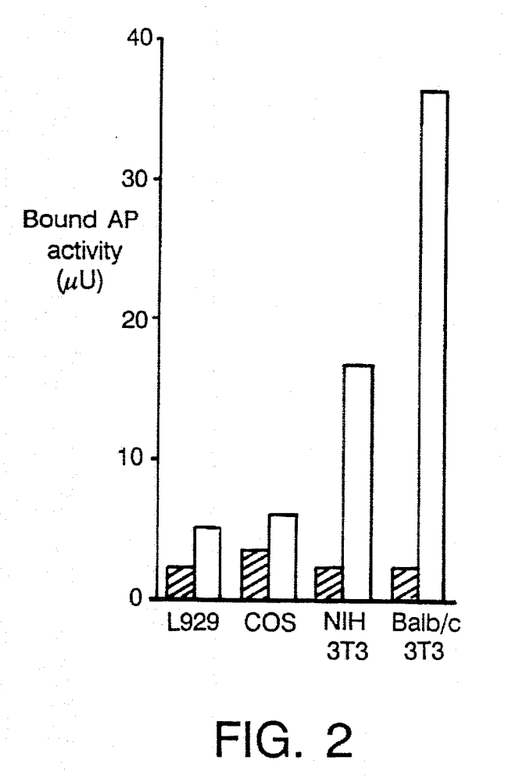
FIG. 2 is a graph showing the binding of APtag-KIT protein to putative ligand-producing cells.

The binding of APtag-KIT protein to L929 (ATCC No. CCL1), COS (ATCC No. CRL 1650), NIH-3T3 (ATCC No. CRL 1658), and Balb/c-3T3 (ATCC No. CCL 163) fibroblasts was tested using the methods described below, and the results of this analysis are shown in FIG. 2. In FIG. 2 putative ◆806Xligand-producing cell lines are listed on the X-axis and the amount of bound AP activity (in μU) is shown on the Y-axis. All four cell lines bound similar amounts of the SEAP protein (striped bars) which was included in the experiment as a control for nonspecific background binding. However, the NIH-3T3 and Balb/c-3T3 cells respectively bound approximately 3-fold and 7-fold more APtag-KIT protein (solid bars) than either the L929 cells or the COS cells. The level of binding to each of the cell lines was reproducible in several independent experiments. The relative binding of APtag-KIT and SEAP is most compatible with only a nonspecific background binding of APtag-KIT by the L929 and COS cells, taking into account the lower concentration of SEAP originally incubated with the cells. Since APtag-KIT binding appeared to parallel the ability of the four cell lines to stimulate mast cell growth, the results suggested that APtag-KIT was binding specifically to a biologically active kit ligand.

Figure 3:
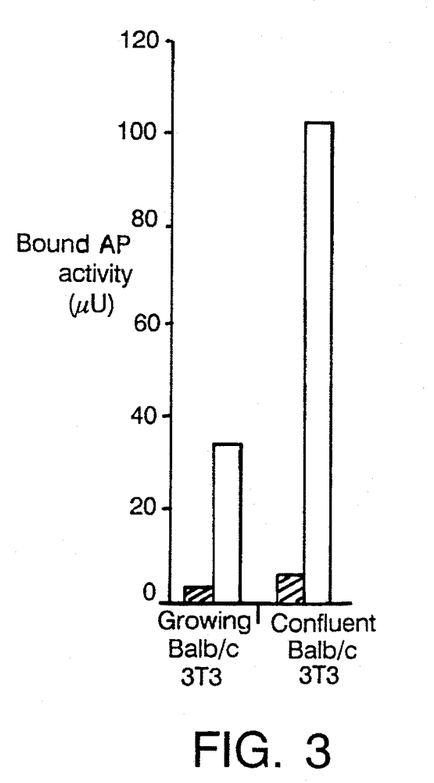
FIG. 3 is a graph showing the binding of APtag-KIT protein to growing and to quiescent Balb/C-3T3 cells.

An additional criterion that should be fulfilled by the kit ligand is that it should be expressed on quiescent cells, since mast cells can be supported for several weeks by a monolayer of confluent, non-dividing 3T3 fibroblasts (Levi-Schaffer et al., *J. Immunol.* 139:3431, 1987; Fujita et al., *Blood* 72:463, 1988, and unpublished observations). Binding of APtag-KIT to quiescent and to growing fibroblast cells was therefore compared using the methods described below and the results of this analysis are shown in FIG. 3. Dividing or quiescent (i.e., confluent for more than 24 hours and no longer dividing) Balb/c-3T3 cells are listed on the X-axis; the amount of bound AP activity (in μU) is shown on the Y-axis). FIG. 3 shows that the APtag-KIT protein (solid bars) bound to the quiescent Balb/c-3T3 cells at levels well above the SEAP control (striped bars). The quiescent culture bound approximately three times more APtag-KIT protein than the dividing culture, though this difference was presumably due at least in part to the greater number of cells (about two-fold higher) in the confluent culture.

APtag-KIT binding was assayed by growing fibroblasts to two-thirds confluence on 60 mm plates, washing cells with HBHA buffer [Hank's balanced salt solution with 0.5 mg/ml BSA (Sigma cat.no. A-7638, St. Louis, Mo.), 0.1% NaN$_3$, 20 mM HEPES pH 7.0], and incubating for 90 min. at room temperature with either J558.AK supernatants (690 mU/ml AP activity) or J558.AP supernatants (330 mU/ml AP activity) containing 0.1% NaN$_3$, 20 mM HEPES pH 7.0, or alternatively with purified APtag-KIT protein in HBHA buffer. Cells were then rinsed seven times with HBHA over a period of 10 min., lysed in 500 μl of 1% the non-ionic surfactant TRITON™ X-100 (octoxynol-9), 10 mM Tris-HCl pH 8.0, and after transferring the lysate to a microfuge tube, the plate was rinsed with an additional 400 μl of the same solution, and the rinsate was also transferred to the microfuge tube. After vortexing vigorously, nuclei were removed by microcentrifugation for 5 min., and the supernatants were heated for 10 min. at 65° C. to inactivate cellular phosphatases. Lysates could be assayed directly at this point, although generally (and for the work described herein) the very slight remaining cellular phosphatase activity was eliminated by immunoprecipitation as follows. Excess monoclonal antibody against placental alkaline phosphatase (cat.no. A-018-01, Medix Biotech, Foster City, Calif.; an antibody with higher affinity than A-018-02) coupled to CNBr-Sepharose 4B beads (as described above) was added to the supernatant, the mixture rotated on a labquake (Labindustries Inc., Berkeley, Calif.) for 90 min. at room temperature, and the beads washed twice in a modified RIPA buffer (0.5% the non-surfactant NONIDET™P-40 (an octylphenol-ethylene oxide condensate containing an average of 9 moles of ethylene oxide per mole of octylphenol), 0.5% NaDOC, 0.025% SDS, 144 mM NaCl, 10 mM Tris-HCl pH 8.0). The beads were then assayed for alkaline phosphatase activity directly on the rotator, using the assay procedure described above. Assays were generally performed at room temperature rather than 37° C. Although the reaction proceeds about half as fast at the lower temperature, this disadvantage can be outweighed by the slower rate of spontaneous chemical hydrolysis of the substrate. Each test of binding was performed with duplicate plates.

APtag-KIT binds saturably and with high affinity to sites on Balb/c-3T3.1 cells

Figure 4:
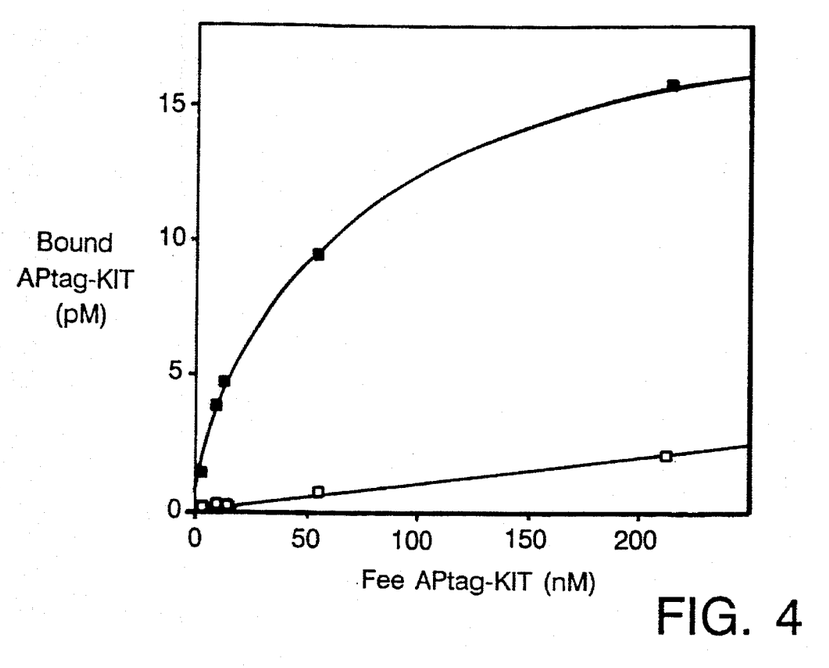
FIG. 4 is a graph of the effect of concentration of APtag-KIT protein on ligand binding.

A typical ligand-receptor interaction is expected to be saturable as the concentration of one of the components is raised to excess, and is expected to be of reasonably high affinity. The results of a binding experiment where cells were incubated with varying amounts of purified APtag-KIT protein is shown in FIG. 4. The Balb/c-3T3 cells used in this and subsequent experiments were from a sub-line, Balb/c-3T3.1, that had spontaneously increased its level of APtag-KIT binding by 5-to 10-fold during culture. The binding analysis was carried out as described above using Balb/c-3T3.1 cells or COS cells, both at two-thirds confluence, and affinity-purified APtag-KIT in varying amounts. In FIG. 4, the amount of bound APtag-KIT protein (in pM) is shown as a function of the amount of free APtag-KIT protein (in nM). The results depicted in this figure demonstrate that binding to Balb/c-3T3.1 cells (filled squares) was saturable with increasing amounts of APtag-KIT protein. The negative control COS cells (open squares) showed much lower levels of binding that did not seem to display saturation.

Figure 5:
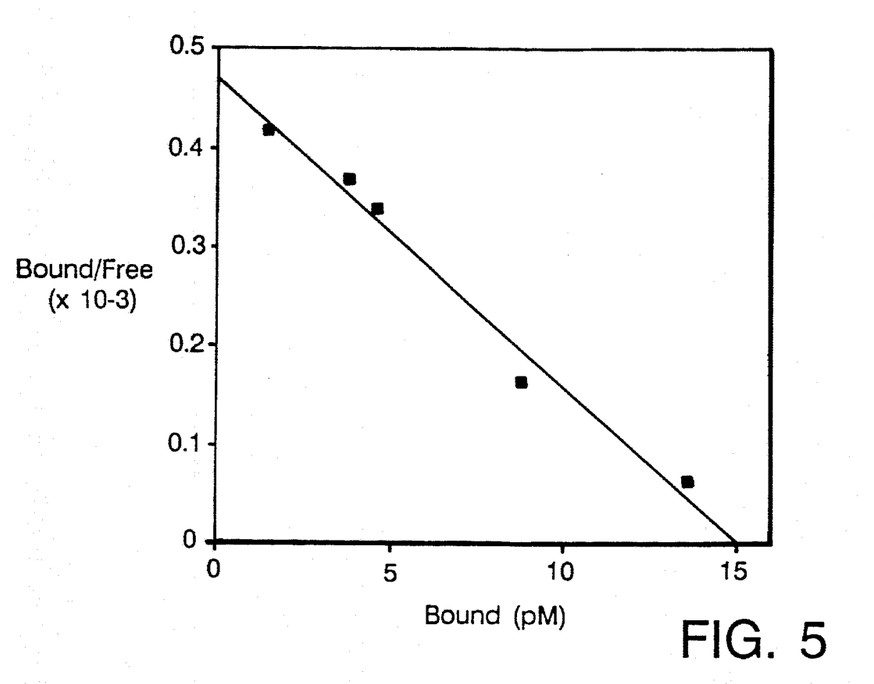
FIG. 5 is Scatchard analysis of the data shown in FIG. 4.

The binding data is presented as a Scatchard plot in FIG. 5, where the X-axis indicates bound APtag-KIT protein (in pM) and the Y-axis indicates (the amount of bound APtag-KIT protein/the amount of free APtag-KIT protein)×10$^{-3}$. The binding data shown in FIG. 4 yield a straight-line Scatchard plot, shown in FIG. 5. Bound values were calculated as (APtag-KIT bound by Balb/c-3T3.1) minus (APtag-KIT bound by COS cells), to compensate for non-specific binding. According to this Scatchard plot, the value for the apparent dissociation constant of the interaction is $K_D=3\times10^{-8}$M and the number of ligand molecules per Balb/c-3T3.1 cell is 20,000. The $K_D$ can also be calculated from the rate constants for binding ($k_{on}$) and dissociation ($k_{off}$), since $K_D=k_{off}/k_{on}$. The rate constants were determined from measurements of the initial rates of association and dissociation of APtag-KIT with Balb/c-3T3.1 cells giving estimates of $k_{off}=1.1\times10^{-2}$min$^{-1}$ and $k_{on}=1.2\times10^{6}$M$^{-1}$min$^{-1}$. These numbers yielded a value for $K_D$ of $0.9\times10^{-8}$M, in good agreement with the value from the Scatchard analysis.

Figure 6:
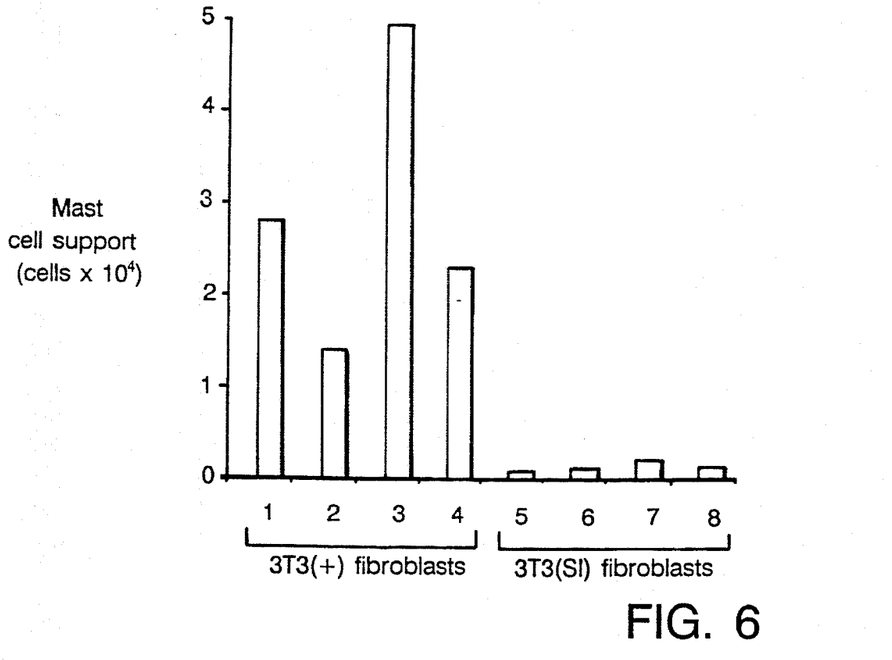
FIG. 6 is a graph of the ability of various fibroblast lines to support mouse mast cell growth.

APtag-KIT binding is reduced in 3T3 fibroblasts cultured from Steel mutant embryos It has previously been found that fibroblasts cultured by the 3T3 protocol from wild-type mouse embryos were reproducibly able to support growth of cultured bone marrow mast cells in in vitro co-culture experiments (Levi-Schaffer et al., *J. Immunol.* 139:3431, 1987; Fujita et al., *Blood* 72:463, 1988; Fujita et al., *Proc. Natl. Acad. Sci. U.S.A.* 86:2888, 1989). In contrast, 3T3 fibroblasts from S1/S1$^d$ embryos (compound heterozygotes for the S1 allele and the slightly milder S1$^d$ allele) could not stimulate mast cell growth (Fujita et al., *Proc. Natl. Acad. Sci. USA* 86:2888, 1989). As shown in FIG. 6, after 1 week of co-culture, far greater numbers of mast cells were present in the cultures with the 3T3 (+) fibroblast lines than with the 3T3 (S1) lines. In this figure, the first four bars (i.e., bars 1–4) represent 3T3 (+) fibroblasts and the second four bars (i.e., bars 5–8) represent 3T3 (S1) fibroblasts; mast cell growth (in cells×10$^4$) is indicated on the Y-axis; solid bars represent APtag-KIT. This analysis was carried out using the methods described below.

Figure 7:
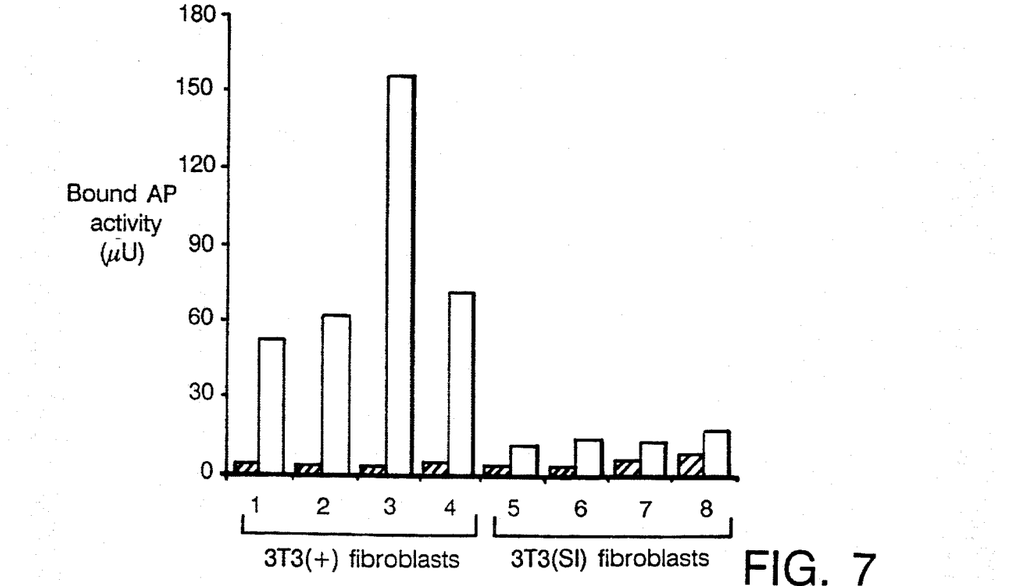
FIG. 7 is a graph of the ability of APtag-KIT protein to bind to putative ligand-producing cells.

The difference in the binding characteristics of APtag-KIT to wild-type or to Steel 3T3 fibroblasts was also investigated. As shown in FIG. 7, binding activity correlated with both the genotype of the fibroblasts and their ability to support mast cell growth. In this figure, the first four sets of bars (i.e., sets of bars 1–4) represent 3T3 (+) fibroblasts and the second four sets of bars (i.e., sets of bars 5–8) represent 3T3 (S1) fibroblasts; the amount of bound AP activity (in μU) is indicated by the Y-axis; solid bars represent APtag-KIT, and striped bars represent SEAP. The analysis was carried out using methods described below. The results shown in FIG. 7 demonstrate that 3T3 (S1) lines bound APtag-KIT at low levels; these low levels may represent only nonspecific background APtag-KIT binding, since similar binding was seen with COS cells and with the SEAP controls, taking into account the lower amount of SEAP initially added. In contrast, the 3T3 (+) lines bound APtag-KIT at levels 4- to 12-fold higher than the average for the 3T3 (S1) lines. These results strongly support the idea that APtag-KIT binds to a biologically-active kit ligand, and provide direct molecular evidence that the Steel locus controls the expression or structure of this ligand.

The 3T3 lines were established as follows: a set of wild-type lines, called 3T3 (+)1 to 3T3 (+)4, was grown from embryos derived from a cross of +/+×+/+ parents, and a set of Steel lines, 3T3(S1)5 to 3T3 (S1)8, was obtained by crossing S1/+×S1/+ parents and selecting embryos that were anemic and therefore likely to be S1/S1 homozygotes. All mice were of the WC/ReJ strain (available from The Jackson Laboratory, Bar Harbor, Me.), which gives relatively good viability of W or S1 mutants (Russell, *Am. J. Med. Genet.* 18:621, 1984). Each 3T3 line was derived from a separate embryo and established by growing, for the 3T3 (+) lines, for 43 to 51 passages and, for the 3T3 (S1) lines, for 48 to 50 passages. Established 3T3 cells were grown to confluence in 35 mm wells, and bone marrow mast cells were added to each well and maintained as described in Fujita et al. *Proc. Natl. Acad. Sci. USA* 86:2888, 1989, hereby incorporated by reference. After one week, the entire culture was trypsinized, and the mast cells were counted in cytocentrifuge preparations stained with toluidine blue as described in *Current Protocols in Molecular Biology*, ed. F. M. Ausubel et al., Greene Publishing Associates and Wiley, New York, N.Y. 1987, hereby incorporated by reference.

In the APtag-KIT binding studies, plates of cells that had been confluent for less than 12 hours were incubated with J558L supernatants containing APtag-KIT (690 mU/ml AP activity) or SEAP (330 mU/ml AP activity). Cells were washed and assayed for bound AP activity as described above. Each AP activity value was the average of duplicate plates.

In situ analysis using the APtag-KIT molecular affinity reagent

Since it appeared that APtag-KIT protein bound to a ligand on the surface of 3T3 fibroblasts, it was of interest to examine the distribution of the bound APtag-KIT protein by in situ staining. Balb/c-3T3.1 and COS cells were plated together and stained with APtag-KIT, as described below. Specific staining was observed only over the Balb/c-3T3.1 cells, which could be identified by their morphology (i.e., the BALB/c-3T3 cells, were more elongated and had smaller and less rounded nuclei than the COS cells). Control COS cells showed darkly staining granules in the perinuclear region but this was evidently due to endogenous cellular phosphatases, since COS cells treated with APtag-KIT and stained were indistinguishable from cells stained but not treated with APtag-KIT. These in situ results were consistent with earlier quantitative binding experiments that showed much higher APtag-KIT binding to Balb/c-3T3.1 cells than to COS cells. In situ staining over the Balb/c-3T3.1 cells did not appear to be restricted to any particular area of the cell surface, and where the COS cells and Balb/c-3T3.1 cells were in contact, the staining closely followed the outlines of the Balb/c-3T3.1 cells and did not extend over the COS cells. These results confirm that the ligand appears to be tightly associated with the surface of Balb/c-3T3.1 fibroblasts, and that the assay method is highly specific and can be used for in situ analysis.

Balb/c-3T3.1 and COS cells were plated together at one-twentieth confluence, and allowed to grow to full confluence over a four day period. The cells were then treated with APtag-KIT which had been concentrated 10-fold (by ultrafiltration) (8,100 mU/ml AP activity). Binding and washing were otherwise performed as described above. Cells were then fixed for 30 sec. in 60% acetone, 3% formaldehyde, 20 mM HEPES pH 7.5, and washed twice for 5 min. each in 150 mM NaCl, 20 mM HEPES pH 7.5. Plates were floated on a 65° C. water bath for 10 min. to inactivate cellular phosphatases, cells were rinsed with 100 mM Tris-HCl pH 9.5, 100 mM NaCl, 5 mM $MgCl_2$ and stained for 72 hr. in the same buffer containing 10 mM L-homoarginine, 0.17 mg/ml BCIP and 0.33 mg/ml NBT (Harlow and Lane, *Antibodies: a laboratory manual*, Cold Spring Harbor Laboratory, Cold Spring Harbor, N.Y., 1988, hereby incorporated by reference).

Capture of KIT-specific ligand

Figure 8:
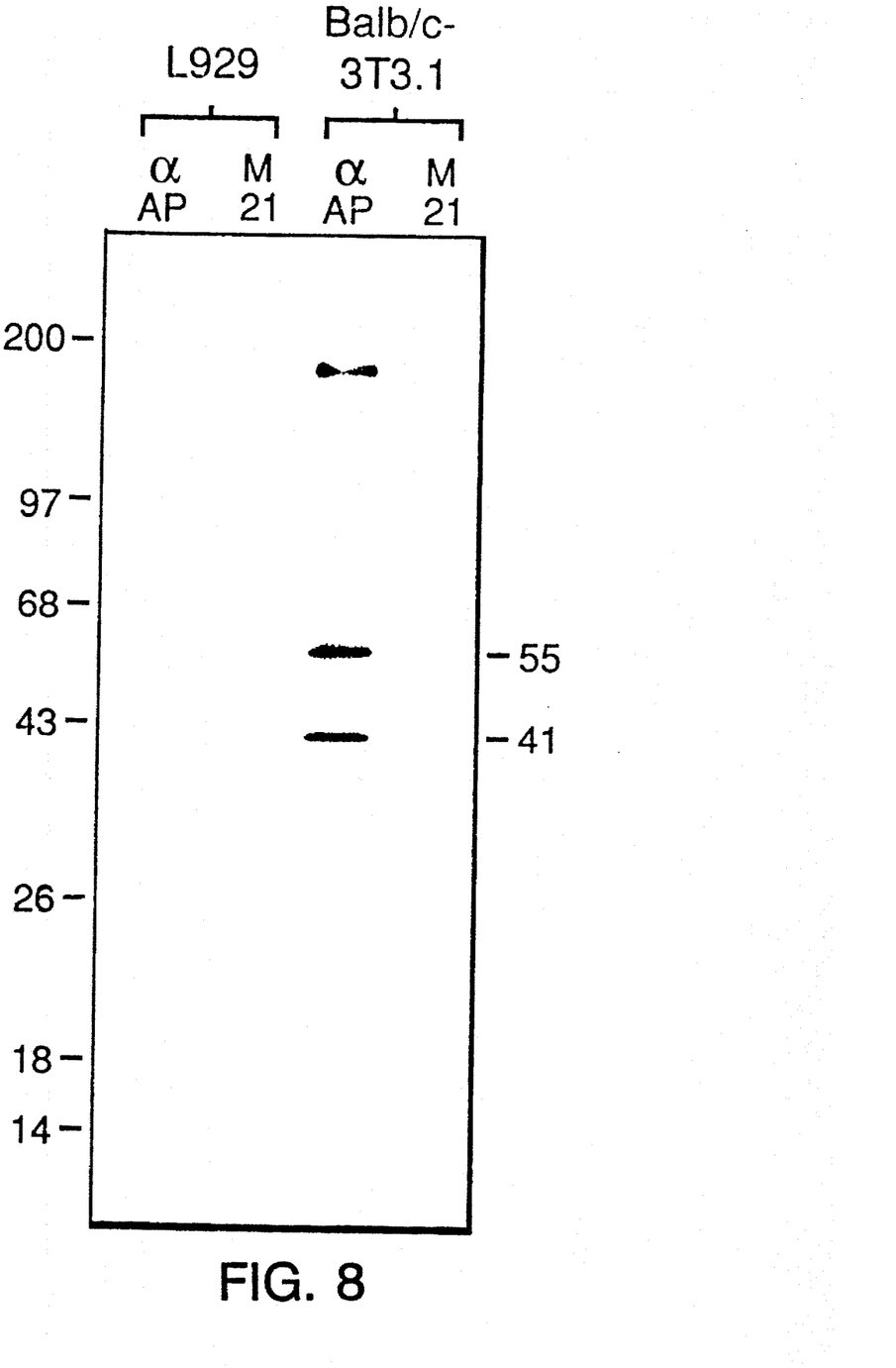
FIG. 8 is a gel showing the mobility and molecular weight of the c-kit ligand.

The availability of APtag-KIT as a high-affinity binding reagent allowed isolation of the mouse c-kit ligand and characterization of its structure. Balb/c-3T3.1 fibroblasts, which bind relatively high amounts of APtag-KIT, and L929 fibroblasts, which do not seem to bind more than non-specific background levels were metabolically labeled with $^3$H-leucine and $^3$H-lysine. The cells were then incubated with concentrated APtag-KIT, incubated with a cleavable crosslinking agent, and lysed. The lysates were immunoprecipitated with an antibody to alkaline phosphatase or with a control antibody, and the immunoprecipitates analyzed by SDS-PAGE, all as described below. Two prominent bands, migrating at 41kD and 55kD, were visualized after the Balb/c-3T3.1 cell lysate was immunoprecipitated with the alkaline phosphatase antibody (FIG. 8, lane 3), but not after this lysate was immunoprecipitated with the control antibody. (FIG. 8, lane 4) These bands were absent from immunoprecipitates of L929 fibroblast lysates (FIG. 8, lanes 1 and 2) and were also absent, in a separate experiment, when antibody to placental alkaline phosphatase was used to precipitate lysates in the absence of APtag-KIT. The detection of two polypeptides could have various explanations. It may suggest that the ligand is a two-chain protein, that it consists of one chain that can associate with an accessory protein, or that it may have multiple forms arising from the same gene but subject to differential RNA splicing or protein processing.

Semiconfluent monolayers of fibroblasts in 100 mm dishes were incubated for 8 hr. in leucine-and lysine-free medium containing 10% dialyzed bovine calf serum, and 50 µCi/ml each of $^3$H-leucine and $^3$H-lysine (New England Nuclear, Boston, Mass.). APtag-KIT binding was carried out using 10-fold concentrated fusion protein (8100 mU/ml AP activity) as described for in situ staining, except that the cells were washed three times in HBHA, then three times in HBS (150 mMNaCl, 20 mM HEPES pH 7.0). Cells were then incubated for 60 min. at 4° C. with 100 µg/ml of the cleavable crosslinking agent DSP (Pierce, Rockford, Ill.) in HBS. The reaction was terminated by washing twice in TBS (150 mM NaCl, 20 mM Tris-HCl pH 8.0), cells were lysed in TBS containing 0.5% the non-ionic surfactant NONIDET™ P-40 (an octylphenyl-ethylene oxide condensate containing an average of 9 moles of ethylene oxide per mole of octylphenol) (Kodak, Rochester, N.Y.) and 1 mM phenylmethylsulphonylfluoride (PMSF) (Sigma, St. Louis, Mo.), and lysates were immunoprecipitated using either Sepharose 4B beads CnBr-coupled to monoclonal alkaline phosphatase antibody or Sepharose 4B beads CnBr-coupled to a control antibody (IgG from myeloma MoPC21) as described above, except that the beads were washed twice with TBS/0.1% the non-ionic surfactant, NONIDENT ™ P-40 (an octylphenyl-ethylene oxide) condensate containing an average of 9 moles of ethylene oxide per mole of octylphenol, three times in RIPA, and once in TBS/0.1% the non-ionic surfactnat NONIDET™ P-40 (an octylphenyl-ethylene oxide condensate containing an average of 9moles of ethylene oxide per) mole of octylphenol). Alternatively, the ligand was immunoprecipitated without employing a chemical crosslinking agent (with similar results). Cells were grown and labelled and treated with the APtag-KIT protein as described above, then washed twice with TBS and lysed with TBS containing 0.5% the nonionic surfactant NONIDET™ P-40 (an octylphenol-ethylene oxide condensate containing an average of 9 moles of ethylene oxide per mole of octylphenol) and 1 mM PMSF. Lysates were vortexed vigorously, and the nuclei and other debris were removed by microcentrifugation for 10 min. The lysates were then immunoprecipitated using Sepharose 4B beads CNBr-coupled to a monoclonal alkaline phosphatase antibody or Sepharose 4B beads CNBr-coupled to a control antibody (IgG from myeloma MoPC21), as described above. The beads were then washed six times with TBS containing a 0.1% the nonionic surfactant NONIDET™ p-40 (an octylphenol-ethylene oxide condensate containing an average of 9 moles of ethylene oxide per mole of octylphenol. Immunoprecipitates obtained by either of the above procedures, were boiled for 2 min. in loading buffer containing 1% β-mercaptoethanol and analyzed by SDS-PAGE on a 5–20% gradient gel, which was subsequently exposed to X-ray film after treatment with Enlightening (Dupont, Wilmington, Del.).

Other Embodiments

Other embodiments are within the following claims. For example, the covalent bond between the receptor and the first member of the specific binding pair may be formed by a chemical reaction such as periodate oxidation coupling or cyanogen bromide coupling. These reactions can be carried out by standard techniques known to those skilled in the art. The receptor portion of the hybrid molecule may be any known or yet unknown receptor ligand-binding domain. A approach similar to that revealed in the preferred embodiment could be used to capture and assay the ligands of other receptors such as those encoded by the neu, ros, met, and trk genes.

The hybrid molecule may be used to capture or assay a ligand using other techniques of affinity complex isolation or detection. The hybrid molecule would functionally replace the more conventionally-utilized antibody molecule. By this method, detection could be accomplished using a single reagent, e.g., a hybrid molecule which includes a receptor for the ligand covalently bound to the first member of a specific binding pair and which is capable of binding both (1) a ligand and (2) a second member of the specific binding pair which undergoes a demonstrable change upon interaction with the first member of the specific binding pair.

The interaction between the members of the specific binding pair that is used to isolate a ligand is not limited to the situation where the members are an antibody and antigen. The members of the specific binding pair, e.g., may be an enzyme and the enzyme's substrate. This would allow the ligand to be purified by conventional methods of molecular separation, e.g., column chromatography, using the enzyme's activity as a marker for the presence of the enzyme. Likewise the activity of the enzyme, i.e., its interaction with its substrate, can be used to signal the presence of the ligand in various in situ techniques, e.g., in tissue sections, or in various in vitro techniques, e.g., in Western blots.

Capture may involve attaching the hybrid molecule to a solid support such as a column and using such a hybrid molecule-linked solid support as an affinity matrix to bind the ligand. The hybrid molecule may be attached to the solid support through a member of the specific binding pair. One particularly useful example would use, as the second member of the specific binding pair, an antibody specific for the first member of the specific binding pair. For example, the hybrid molecule could include the receptor bound to an enzyme and the hybrid molecule could be attached to the support by an antibody directed against the enzyme. A hybrid molecule which includes an alkaline phosphatase moiety can be bound to a solid support using available monoclonal antibodies (e.g., those antibodies described above). Elution from such a solid support is accomplished under mild conditions, e.g., by adjusting the pH to 5.5.

Alternatively, the hybrid molecule may be attached to a substrate analog matrix, wherein the substrate analog represents the second member of the specific binding pair and the enzyme which recognizes the substrate analog represents the first member of the specific binding pair. Under appropriate conditions, the enzyme moiety (and, thus, the hybrid molecule) remains physically associated with the substrate analog matrix because the analog is bound, but not acted upon, e.g., cleaved, by the enzyme. Techniques for using known substrate analogs or for making novel substrate analogs are well known to those skilled in the art. In one particular example, a hybrid molecule which includes an alkaline phosphatase moiety can be bound to a solid support bearing phosphonic acid residues and can be eluted with low concentrations of phosphate (e.g., as described by Landt et al., *Biochemistry* 17:915, 1978).

Methods of the invention also allow for the rapid and convenient assay of the ability of a substance, e.g., a drug or other therapeutic agent, to block binding between a ligand and a receptor. For example, an assay for the ability of a drug to block the interaction between gp120 (a protein found on the surface of HIV) and CD4 (the receptor for the gp120 protein) could be performed by placing CD4 bearing cells on a substrate, contacting the CD4-bearing lymphocytes with the drug and with a SEAP-CD4 hybrid molecule, e.g., APtag-CD4, washing the cells to remove unbound SEAP-CD4, and staining for alkaline phosphatase activity. A decreased level of bound alkaline phosphatase activity, as compared to the level in a control not contacted with the drug, would indicate that that drug was capable of blocking the CD4-gp120 interaction. Other agents may also be tested for their ability to interfere with a ligand receptor interaction. For example, fragments of the c-kit ligand or the c-kit receptor which block a wild-type c-kit receptor-ligand interaction could be identified. Generally, this approach could be used to identify therapeutic agents which block the interaction between any receptor, e.g., an oncogene receptor, and its ligand.

Possession of a ligand, e.g., the c-kit ligand, allows one of ordinary skill in the art to obtain the DNA sequences encoding the ligand. For example, one skilled in the art could use the protein precipitated from Balb/c-3T3 cells and resolved into its subunits by SDS-PAGE, to obtain the N-terminal sequence of each of the subunits. The N-terminal sequences could be used to make synthetic oligonucleotides, which could be used to obtain cDNAs encoding the subunits, e.g., by screening a cDNA library from Balb/c-3T3 cells. This approach can be applied to any ligand isolated by methods of the invention.

Availability of the human c-kit receptor gene (Yarden et al., *EMBO J.* 6:3341, 1987, hereby incorporated by reference) would allow one skilled in the art to produce a molecular affinity reagent (e.g., an APtag-Human Kit hybrid molecule) using the methods described above; this affinity reagent could then be used to isolate the human c-kit ligand, also as described above. Alternatively, the methods and molecules of the invention could be used to isolate the human c-kit ligand as follows. The ability of the mouse c-kit ligand to bind the human c-kit receptor is very strongly suggested by the observation that the growth of human mast cells in vitro is supported by c-kit ligand-producing mouse fibroblasts, see e.g., Furitsu et al., *Proc. Natl. Acad. Sci. USA* 86:10039, 1989; and Levi-Schaffer et al., *J. Immunol.* 13:9:494, 1987. If the mouse c-kit receptor binds the human ligand (as suggested by the observation that the mouse ligand seems likely to bind the human receptor) an affinity reagent including the mouse c-kit receptor covalently coupled to a member of a binding pair, e.g., SEAP, could be used to identify and isolate a human c-kit ligand. Alternatively, the DNA sequence of the mouse c-kit ligand could be used to isolate DNA encoding the human analogs. Homology at the binding domain is very strongly suggested by the mast cell support studies cited above, and this homology may be exploited by one skilled in the art to isolate the homologous human gene (e.g., from a human fibroblast cDNA library).

Isolation of the c-kit ligand gene allows one skilled in the art to insert this gene into a vector (e.g., a vector designed to express the ligand, preferably in large quantities) using standard techniques of recombinant DNA technology. The ligand can be produced from cells which naturally express the protein or from cells harboring a c-kit ligand-expression vector (obtained by introducing a c-kit ligand expression vector into a host cell using standard techniques, e.g., transfection, electroporation, or infection by viral vectors). The protein would be isolated using methods of the invention or any standard purification procedure.

The c-kit ligand is a growth factor for cells involved in the early stages of hematopoiesis (see, for example, Russell, *Am. J. Med. Genet.* 18:621, 1984; Silvers, The coat colors of mice: a model for gene action and interaction., Springer-Verlag, 1979; Landreth et al., *J. Immunol.* 132:2724, 1984) and, thus, administration of the c-kit ligand could be used to stimulate proliferation of hematopoietic cells in vitro (e.g., to enhance the growth of cultured cells) or in vivo (e.g., to promote the survival of transplanted bone marrow cells or to stimulate hematopoietic cell proliferation in an individual suffering from hematopoietic deficiencies, e.g., anemia or AIDS, or in a patient following dialysis). For in vitro administration, the ligand may be added directly to the supernatant of cultured cells in an amount sufficient to stimulate cell proliferation. For in vivo administration, a therapeutically-effective amount of a soluble form of the ligand may be administered, e.g., intravenously, to a patient requiring treatment. Alternatively, the ligand may be expressed from a gene which is introduced into the appropriate somatic cells of the patient. In one particular example, cells which normally produce the ligand (e.g., bone marrow cells) are isolated from a patient and transfected with a vector which directs expression of human c-kit ligand. This construct may be introduced into the patient's explanted cells by any standard transfection technique, e.g., by infection of cells with a non-pathogenic viral vector which expresses the human c-kit ligand gene. The ligand-producing cells would then be returned to the patient, e.g., by injection back into the patient's bone marrow. Because the ligand may be expressed in a form that remains on the surface of the transfected cell, this approach may permit stimulation of appropriate hematopoietic cells while minimizing or eliminating stimulation of inappropriate cells (e.g., mast cells). This would reduce the likelihood of possible side effects (e.g., anaphylactic shock) which might result from therapy involving the soluble form of the ligand. A similar approach may be used to express an antagonist, e.g., a mutant ligand or receptor, on the surfaces of the appropriate cells for the purpose of blocking interactions between wild-type ligands and receptors (e.g., the c-kit ligand and receptor).

A substance shown to block ligand-receptor binding could be used to block viral infection (e.g., infection of cells by HIV-1) or to inhibit cell growth dependent on such an interaction (e.g., neoplasias dependent for their growth on an excess of receptor, an excess of a ligand, or a sustained receptor-ligand interaction). In one particular example, the c-kit ligand has been shown to be involved in the proliferation of melanocytes, and thus, blocking the interaction between the c-kit ligand and its receptor could be used to inhibit the growth of melanocyte-related cancers.

We claim:

1. A method of isolating a ligand of a known polypeptide receptor from a sample, said method comprising
providing a hybrid molecule comprising said polypeptide receptor covalently bonded to SEAP,
contacting said sample with said hybrid molecule to form an affinity complex between said ligand and said hybrid molecule, and
isolating said affinity complex using a molecule which binds SEAP.

2. The method of claim 1, wherein said covalent bond is a peptide bond.

3. The method of claim 1, wherein said ligand is soluble.

4. The method of claim 1, wherein said ligand is bound to a cell.

5. The method of claim 1, further comprising contacting said affinity complex with a cross-linking agent to cross-link said ligand to said polypeptide receptor.

6. The method of claim 1, wherein said ligand is a polypeptide.

7. The method of claim 1, wherein said molecule which binds SEAP comprises an antibody that binds to SEAP.

8. The method of claim 1, wherein said polypeptide receptor is a cell surface receptor.

9. The method of claim 8, wherein said cell surface receptor is an oncogene-encoded receptor.

10. The method of claim 9, wherein said oncogene-encoded receptor is a c-kit receptor.

11. The method of claim 10, wherein said c-kit receptor is the human c-kit receptor.

12. The method of claim 8, wherein said cell surface receptor is a viral receptor.

13. The method of claim 12, wherein said viral receptor is an HIV envelope protein receptor.

14. The method of claim 1, wherein said polypeptide receptor comprises a soluble portion of an insoluble peptide.

15. The method of claim 1, wherein said molecule which binds SEAP comprises a substrate analog for said SEAP.

16. A method of detecting a ligand of a known polypeptide receptor in a sample, said method comprising
providing a hybrid molecule comprising said polypeptide receptor covalently bonded to SEAP,
contacting said sample with said hybrid molecule to form an affinity complex between said ligand and said hybrid molecule, and
treating said sample such that any hybrid molecule not forming an affinity complex is removed, and
detecting said affinity complex using a molecule which binds SEAP to detect the presence of said ligand.

17. The method of claim 16, wherein said covalent bond is a peptide bond.

18. The method of claim 16, wherein said ligand is soluble.

19. The method of claim 16, wherein said ligand is bound to a cell.

20. The method of claim 16, further comprising contacting said affinity complex with a cross-linking agent to cross-link said ligand to said polypeptide receptor.

21. The method of claim 16, wherein said ligand is a polypeptide.

22. The method of claim 16, wherein said polypeptide receptor is an oncogene-encoded receptor.

23. The method of claim 22, wherein said oncogene-encoded receptor is a c-kit receptor.

24. The method of claim 23, wherein said c-kit receptor is a human c-kit receptor.

25. The method of claim 16, wherein said polypeptide receptor comprises a soluble portion of an insoluble peptide.

26. The method of claim 16, wherein said molecule which binds SEAP comprises the substrate of said SEAP.

27. The method of claim 16, wherein said molecule which binds SEAP comprises an antibody which binds to said SEAP.

28. The method of claim 16, wherein said detection of said affinity complex allows determination of the distribution of said ligand in said sample.

29. The method of claim 16, wherein said sample is a tissue section.

30. The method of claim 16, wherein said sample is a blot.

31. The method of claim 16, wherein said polypeptide receptor is a cell surface receptor.

32. A method for determining the ability of a molecule to interfere with the binding of a ligand of a known polypeptide receptor to said polypeptide receptor comprising contacting said ligand with said molecule and with a hybrid molecule comprising said polypeptide receptor covalently bonded to SEAP, allowing an affinity complex between said hybrid molecule and said ligand to form, and measuring said affinity complex using a molecule which binds SEAP, the measurement being an inverse measure of said ability.

33. The method of claim 32, wherein said covalent bond is a peptide bond.

34. The method of claim 32, wherein said ligand is soluble.

35. The method of claim 32, wherein said ligand is bound to a cell.

36. The method of claim 32, further comprising contacting said affinity complex with a cross-linking agent to cross-link said ligand to said polypeptide receptor.

37. The method of claim 32, wherein said ligand is a polypeptide.

38. The method of claim 22, wherein said polypeptide receptor is a cell surface receptor.

39. The method of claim 38, wherein said cell surface receptor is an oncogene-encoded receptor.

40. The method of claim 39, wherein said oncogene-encoded receptor is a c-kit receptor.

41. The method of claim 40, wherein said c-kit receptor is human c-kit receptor.

42. The method of claim 38, wherein said cell surface receptor is a viral receptor.

43. The method of claim 42, wherein said viral receptor is an HIV envelope protein receptor.

44. The method of claim 32, wherein said polypeptide receptor comprises a soluble portion of an insoluble peptide.

45. The method of claim 32, wherein said molecule which binds SEAP comprises the substrate of said SEAP.

46. The method of claim 32, wherein said molecule which binds SEAP comprises an antibody which binds to SEAP.

* * * * *